United States Patent [19]

Hohenschutz et al.

[11] 4,217,460
[45] Aug. 12, 1980

[54] ISOLATION OF FORMIC ACID FROM ITS AQUEOUS SOLUTIONS

[75] Inventors: Heinz Hohenschutz, Mannheim; Johannes E. Schmidt, Ludwigshafen; Hans Kiefer, Wachenheim, all of Fed. Rep. of Germany

[73] Assignee: BASF Aktiengesellschaft, Fed. Rep. of Germany

[21] Appl. No.: 893,953

[22] Filed: Apr. 6, 1978

Related U.S. Application Data

[63] Continuation of Ser. No. 725,845, Sep. 23, 1976, abandoned.

[30] Foreign Application Priority Data

Oct. 11, 1975 [DE] Fed. Rep. of Germany ....... 2545658

[51] Int. Cl.² .................... C07C 51/44; C07C 51/48; C07C 53/02
[52] U.S. Cl. ........................... 562/609; 203/DIG. 21; 562/600; 562/606; 562/608
[58] Field of Search ...................... 260/542, 541, 540; 562/608, 609, 606

[56] References Cited

U.S. PATENT DOCUMENTS 2,578,698 12/1951 Hanford .............................. 260/541
3,951,755 4/1976 Sartorius et al. .................... 260/541

Primary Examiner—Vivian Garner
Attorney, Agent, or Firm—Keil & Witherspoon

[57] ABSTRACT

Carboxylic acids of the general formula I

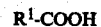

where $R^1$ is hydrogen, methyl, ethyl or vinyl, are isolated from their dilute aqueous solutions by extraction followed by distillation of the mixtures obtained, the extractant used being a secondary amide of the general formula II

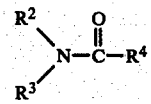

where $R^2$ and $R^3$ are alkyl, cycloalkyl, aryl or aralkyl or conjointly are 1,4- or 1,5-alkylene, in each case of not more than 8 carbon atoms, with the proviso that the sum of the carbon atoms of $R^2$ and $R^3$ is from 7 to 14 and that only one of these radicals is aryl, and where $R^4$ is one of the radicals $R^1$.

6 Claims, No Drawings

ISOLATION OF FORMIC ACID FROM ITS AQUEOUS SOLUTIONS

This is a continuation of application Ser. No. 725,845 filed Sept. 23, 1976, now abandoned.

The present invention relates to a new process for isolating carboxylic acids of the general formula I $$R^1\text{-COOH} \qquad \qquad I$$

where $R^1$ is hydrogen, methyl, ethyl or vinyl, from their aqueous solutions.

A number of syntheses result in carboxylic acids I being obtained in the form of their dilute aqueous solutions. Experience has shown that if it is desired to isolate the pure or concentrated acids therefrom, substantial technical difficulties are encountered. Removal of the water by distillation which in the case of formic acid is in any case not possible at commercially acceptable expense, because of azeotrope formation, requires in all other cases both a large amount of energy and expensive distillation columns with numerous trays, since the degree of separation of the acid/water system achieved by a single tray is slight.

It is true that the water can be removed more rapidly, and with less expensive equipment, by azeotropic distillation with a water-insoluble liquid such as ethyl acetate or benzene, but this of course requires even more energy than a simple distillation.

For these reasons, numerous separation processes have been developed, which are based on the extraction of the acid with a liquid extractant such as isoamyl acetate or methyl isopropyl ketone.

However, the efficiency of the extractants of the prior art is not fully satisfactory, since the extractants take up insufficient acid and too much water. Hence, mixtures of extractants, acid and water are obtained in every case and these, in turn, require relatively expensive further processing since, in the case of none of these extractants can the three components be separated by simple distillation.

It is an object of the present invention to increase the efficiency of extraction of a carboxylic acid I from its dilute aqueous solutions, by providing more suitable extractants.

We have found that this object is achieved and that carboxylic acids of the general formula I $$R^1\text{-COOH} \qquad \qquad I$$

where $R^1$ is hydrogen, methyl, ethyl or vinyl, can be obtained by extracting their dilute aqueous solutions and then distilling the mixtures obtained, if the extractant used is a secondary amide of the general formula II

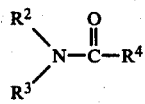

where $R^2$ and $R^3$ are alkyl, cycloalkyl, aryl or aralkyl or conjointly are 1,4- or 1,5-alkylene, in each case of 1 to 8 carbon atoms, with the proviso that the sum of the carbon atoms of $R^2$ and $R^3$ is from 7 to 14 and that only one of these radicals is aryl, and where $R^4$ is one of the radicals $R^1$.

Since a trans-amidation with the acid I can take place, extractants where $R^4$ and $R^1$ are identical are always preferred. Accordingly, formic acid is advantageously extracted with a formamide, acetic acid with an acetamide, propionic acid with a propionamide and acrylic acid with an acrylamide II, so that the occurrence of the trans-amidation is outwardly not detectable. If it is intended to isolate mixtures of different acids, e.g. formic acid and acetic acid, it is preferred to use the compounds of the formamide series, as being the most efficient compounds of the category which has been defined.

From the point of view of the amide groupings, particularly suitable compounds II, and their mixtures, are those derived from N-ethyl-N-cyclohexylamine, N,N-dicyclohexylamine, N-methyl-N-benzylamine, N-methylaniline, N-ethylaniline, N,N-diamylamine, N-methyl-N-2-ethylhexylamine, N-n-butyl-N-cyclohexylamine, N-methyl-N-2-heptylamine or N-propyl-N-cyclohexylamine. The dibutylformamides, including above all di-n-butylformamide, have proved best for formic acid, and N-n-butyl-N-2-ethylhexylacetamide and N-n-butyl-N-cyclohexylacetamide have proved best for acetic acid.

The amides II are either known compounds or are readily accessible by conventional methods. If their freezing point is above the extraction temperature, it is necessary to use mixtures of the extractants II, or to work in the presence of a solvent, preferably an aromatic hydrocarbon such as p-diisopropylbenzene, which does not form an azeotrope with the acids. It is true that in this variant the efficiency of the extractant II is reduced, but nevertheless sufficient advantages over conventional methods remain, since the amount of solvent normally required to lower the freezing point is low, namely from 10 to 40% by weight, based on II.

The partition coefficient, which is defined in Example 3 and is quoted for several acid/extractant systems, is a measure of the suitability of the extractants. The lower is this coefficient, the greater the expense of the equipment required for the extraction. However, it is not only the partition coefficient for the acid but also the partition coefficient for water which has to be taken into account, since, naturally, the isolation of pure or concentrated acid requires less energy if the extractant takes up very little water; this latter condition is fulfilled satisfactorily by all of the extractants of the invention.

The requisite amount of extractant II depends on various parameters, including, above all, the temperature, the amount and concentration of acid, the number of separation stages and the other details of the equipment which affect equilibration and hence affect the residence time. The amount of extractant II required does not vary fundamentally with the particular extractant used and the particular acid involved.

The preferred temperature range for the extraction is from 0° to 70° C. It is true that at the lower end of this range, the extractant can absorb more acid than at higher temperatures, but on the other hand the rate of equilibration is lower. The economic optimum is in the range of from 20° to 40° C.

In the range of from 20° to 40° C., from 1 to 10 kg of extractant II are normally required for extracting 1 kg of acid at a contact time of from 1 to 5 minutes. The amount of extractant is less for longer contact times and vice versa. The stated contact times apply to the preferred embodiment of counter-current extraction, in a simple extraction column without other auxiliaries such as baffles, trays or packing, and under conditions where the lighter extractant forms the continuous phase. The efficiency is increased by using multi-stage extraction apparatus, e.g. packed columns or tray columns with, preferably, from 3 to 6 theoretical plates, so that the amount of the extractant can be reduced in accordance with the conventional rules.

The above data relate to acid concentrations of from 5 to 50% by weight of the aqueous solution, these being the most commonly encountered concentrations in industry. The depletion ratio, of from 95 to 99% by weight, is relatively constant, i.e. if the initial solution is of 30% strength, from 0.1 to 0.3% of acid remain in the aqueous medium, whilst if a 10% strength solution is extracted, a solution containing from 0.05 to 0.1% of acid remains. In general, it is most economical to take the extraction to the point that a mixture of the extractant and an acid of from 10 to 40 percent strength by weight is obtained. The water is then distilled from this mixture, after which the acid is distilled off in a downstream column. It is also possible, using conventional methods, to use an arrangement where only a part of the water is removed in the first column, whilst in the second column the residual water is distilled off together with the acid. In that case, a commercial concentrated acid is obtained instead of the pure acid.

The above comments relate to the continuous manufacture of carboxylic acids I, which in industry is virtually the only embodiment of importance. However, the process can of course also be carried out batchwise, if desired, in which case the general sense of the conditions outlined above must be adhered to.

It should be pointed out that the feature of the process which is essential to the invention is the nature of the extractant, and not the extraction technique used, which is the conventional technique. To that extent, the conditions outlined merely represent guidelines, from which it is possible to deviate, in individual cases, in accordance with conventional rules and the conventional process technology, should this be advisable; an example is the treatment of effluent, where the purification of the water is more important than the isolation of the acid. Furthermore, it is possible to use the stated extractants for the extractive distillation of the aqueous acids.

The present process permits a substantial saving in energy and investment costs, both in comparison to other extraction processes and in comparison to distillative treatment. It particularly represents an advance where the isolation of pure or concentrated formic acid or acetic acid is concerned, and where aqueous solutions which contain several acids I have to be worked up.

EXAMPLE 1

1 kg per hour of a 21 percent strength by weight aqueous formic acid, as obtained by industrial synthesis from methanol and carbon monoxide, was fed, at from 20° to 25° C., into the top of a packed column into which 0.9 kg per hour of di-n-butylformamide was fed, in counter-current, at the bottom. The extractant formed the continuous phase.

1.2 kg per hour of extract phase were taken off a settling zone at the upper end of the column; this phase contained virtually all the formic acid (210 g), together with 90 g of water, i.e. 300 g of 70% strength formic acid. This acid was separated from the extractant by simple continuous distillation in a packed column at 45° C. (column top temperature) and 60 mm Hg.

The extractant, which still contained traces of formic acid, was recycled from the bottom of the distillation column to the extraction column.

In order to obtain formic acid of about 90 percent strength by weight, 70 g per hour of water were distilled from the extract phase first obtained, in a packed column (atmospheric pressure, bottom temperature 143° C.), after which the mixture remaining in the bottom of this column was subjected to a second distillation in a column with 25 bubble-cap trays, at 60 mm Hg and 42° C. (column top temperature), giving a 90% strength acid as the distillate.

Using a similar method and employing the two columns, virtually anhydrous formic acid was obtained from the 90% acid.

EXAMPLE 2

1 kg per hour of a 15 percent strength by weight aqueous acetic acid was fed, at room temperature, into the top of a column with 12 sieve trays, whilst 0.75 kg per hour of N-n-butyl-N-2-ethylhexylacetamide were fed in at the bottom. 81 percent strength by weight acetic acid and anhydrous acetic acid were produced, by the method described in Example 1, from the extract phase, which contained virtually all the acetic acid, together with 4% by weight of water.

EXAMPLE 3

Since the suitability of the extractants depends above all on the partition coefficient $$C = \frac{\text{concentration of the acid in the organic phase}}{\text{concentration of the acid in the aqueous phase}}$$

these coefficients were determined, for the practical requirements of the present process, by stirring 100 g of the extractant with 143 g of a 30 percent strength by weight acid (corresponding to 100 g of water) at 25° C., until equilibrium was reached. The quotient C was then calculated from the acid concentrations in the organic phase and in the aqueous phase.

The Table which follows gives a survey of the partition coefficients of some extractants according to the invention, and, by way of comparison, of some conventional extractants.

F=formic acid
A=acetic acid
P=propionic acid
Acr=acrylic acid

| Extractant | Acid | Partition coefficient C |
|---|---|---|
| according to the invention | | |
| N-Di-n-butylformamide | F | 1.12 |
| | A | 1.39 |
| | P | 4.60 |
| | Acr | 6.91 |
| N-Di-n-butylacetamide | F | 1.33 |
| N-Methyl-N-2-heptylformamide | F | 1.18 |
| N-n-Butyl-N-2-ethylhexylacetamide | A | 1.07 |
| N-n-Butyl-N-cyclohexylacetamide | A | 1.39 |
| 50% by weight of N-di-n-butylformamide + 50% by weight of N-di-cyclohexylformamide | F | 1.04 |
| 67% by weight of N-di-n-butylacetamide + 33% by weight of N-dicyclohexylacet- | | |

| Extractant | Acid | Partition coefficient C |
|---|---|---|
| amide | A | 1.44 |
| 80% by weight of N-di-n-butylformamide + | | |
| 20% by weight of p-diisopropylbenzene | F | 0.98 |
| N-Ethyl-N-cyclohexylformamide | F | 1.26 |
| N-Ethylformanilide | F | 0.96 |
| N-Dibutylpropionamide | P | 4.02 |
| conventional | | |
| Benzene | F | 0.006 |
|  | A | 0.115 |
| Methylene chloride | F | 0.014 |
|  | A | 0.25 |
| Trichloroethylene | F | 0.002 |
|  | A | 0.074 |
| Diisopropyl ether | F | 0.267 |
|  | A | 0.39 |
| Isobutyl acetate | F | 0.34 |
|  | A | 0.56 |
| Methyl isopropyl ketone | F | 0.84 |
|  | A | 1.07 |
|  | P | 2.82 |
|  | Acr | 3.49 |
| Cyclohexyl formate | F | 0.31 |
| Cyclohexanol | F | 0.38 |

We claim:

1. A process for isolating formic acid from its aqueous solutions which comprises first extracting an aqueous solution of formic acid with a liquid extractant and then distilling the formic acid from the extractant mixture thus obtained, using as said liquid extractant a dialkyl formamide of the formula

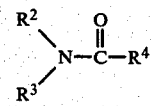

wherein:
$R^2$ and $R^3$ are alkyl groups of up to 8 carbon atoms with the proviso that the sum of the carbon atoms of $R^2$ and $R^3$ is from 7 to 14; and
$R^4$ is hydrogen.

2. A process as claimed in claim 1 wherein the extraction is carried out at a temperature of from about 0° to 70° C.

3. A process as claimed in claim 1 wherein the extraction is carried out at a temperature of from about 20° to 40° C.

4. A process as claimed in claim 3 wherein from 1 to 10 kg of extractant are used per kilogram of said acid at a contact time of from about 1 to 5 minutes.

5. A process as claimed in claim 1 wherein $R^2$ and $R^3$ taken with the nitrogen atom as the amido substituents are selected from the group consisting of:
N,N-diamyl;
N-methyl-N-2-ethylhexyl;
N-methyl-N-2-heptyl and
N,N-di-n-butyl.

6. A process as claimed in claim 1 wherein N,N-di-n-butylformamide is employed as the extractant for said formic acid.

* * * * *